United States Patent [19]

Chabardes et al.

[11] Patent Number: 5,202,497
[45] Date of Patent: Apr. 13, 1993

[54] PROCESS FOR PREPARING UNSATURATED ALDEHYDES

[75] Inventors: Pierre Chabardes, Sainte Foy Les Lyon; Serge Henrot, Saint Genis Laval, both of France

[73] Assignee: Rhone-Poulenc Nutrition Animale, Commentry, France

[21] Appl. No.: 863,455

[22] Filed: Apr. 1, 1992

[30] Foreign Application Priority Data

Apr. 2, 1991 [FR] France ................................ 91 03946

[51] Int. Cl.$^5$ ...................... C07C 45/00; C07C 45/27; C07C 209/00
[52] U.S. Cl. .................................... 568/436; 568/420; 568/426; 568/449; 564/305; 564/463
[58] Field of Search ............... 568/420, 426, 436, 449; 564/500, 305, 463

[56] References Cited

PUBLICATIONS

M. N. Sheng et al. "Hydroperoxide Oxidations Catalyzed by Metals. II. The Oxidation of Tertiary Amines to Amine Oxides," Journal of Organic Chemistry, vol. 33, No. 2, 1968, pp. 588–590.
R. V. Hoffman, "The Oxidation of Amines with Sulfonyl Perioxides," Journal of the American Chemical Society, vol. 98, No. 21, 1976, pp. 6702–6704.
K. Takabe et al., "A Simple Conversion of N,N-Dimethyl-2-Alkenylamine to 2-Alkenal," Chemistry Letters, No. 12, 1982, pp. 1987–1988.
S. Murahashi et al., "Ruthenium-Catalyzed Cytochrome P-450 Type Oxidation of Tertiary Amines With Alkyl Hydroperoxides," Journal of the American Chemical Society, vol. 110, No. 24, 1988, pp. 8256–8258.
M. N. Sheng et al., "N,N-Dimethyldodecylamine Oxide," Organic Synthesis, vol. 50, 1970, pp. 56–62.
Rawalay et al "Journal of Organic Chemistry", vol. 32 No. 10 pp. 3129–3131 (Oct. 1967).

*Primary Examiner*—Werren B. Lone
*Attorney, Agent, or Firm*—Finnegan, Henderson, Farabow, Garrett & Dunner

[57] ABSTRACT

The invention relates to a process for preparing unsaturated aldehydes and their enamines by the oxidation of allylic tertiary amines in the presence of an alkyl hydroperoxide and a vanadium-based catalyst.

22 Claims, No Drawings

PROCESS FOR PREPARING UNSATURATED ALDEHYDES

BACKGROUND OF THE INVENTION

The present invention relates to a process for the synthesis of unsaturated aldehydes. More specifically, it relates to a process for the synthesis of unsaturated aldehydes from allylic tertiary amines It is known in the prior art to prepare tertiary amine N-oxides by oxidation of the corresponding amines in the presence of a hydroperoxide and a metal catalyst. In particular, Sheng et al. (J. Org. Chem. 33:588 (1968); Organic Synthesis 50:56 (1970)) describe the preparation of tri-n-butylamine, triethylamine and 1-dimethylamino-2-propanol N-oxides. In paticular, the metals used are vanadium, molybdenum, chromium, cobalt, iron and manganese; the hydroperoxide being chosen from cumyl and amylene hydroperoxides.

It is also known to carry out the N-dealkylation of tertiary amines in the presence of a ruthenium catalyst and tert-butyl hydroperoxide (Murahashi et al., Am. Chem. Soc. 110:8256 (1988)). This process is especially well-suited to the selective demethylation of tertiary methylamines.

However, none of these documents describes or suggests the possibility of oxidizing tertiary amines directly to aldehydes. Moreover, nothing in these documents suggests the possibility of directly oxidizing allylic tertiary amines, the reactivity of which is different from that of the aliphatic amines described in the prior art.

Applicants have now shown that it is possible to oxidize allylic tertiary amines to form the corresponding unsaturated aldehydes. Moreover, Applicants likewise show that the oxidation also leads to the formation of the corresponding enamine.

SUMMARY OF THE INVENTION

The subject of the present invention lies in a process for preparing an unsaturated aldehyde and its enamine, comprising the step of oxidizing the corresponding allylic tertiary amine in the presence of an alkyl hydroperoxide and a vanadium-based catalyst.

The aldehyde and enamine formed are in a state of equilibrium, which is readily shifted towards the aldehyde when the products are exposed to a dilute acid medium.

DETAILED DESCRIPTION OF THE INVENTION

The allylic tertiary amines which are usable in the present invention correspond, in particular, to the general formula $(R_1)(R_2)N(R_3)$, in which $R_1$, $R_2$ and $R_3$, which may be the same or different, are chosen from Cl to $C_{30}$ alkyl or $C_2$ to $C_{30}$ alkenyl groups, and may be linear, branched, substituted or unsubstituted, cyclic or containing a ring, optionally having one or more hetero atoms, and in which $R_1$ and $R_2$ can form a ring with one another and $R_3$ at least represents an allylic group.

As used in relation to the present invention, allylic group is understood to mean any group having at least one double bond in the $\beta$, $\gamma$-position with respect to the nitrogen atom.

Preferably, $R_1$ and $R_2$, which may be the same or different, are linear or branched alkyl groups containing 1 to 4 carbon atoms and capable of forming a ring or a heterocycle with one another.

Still more preferably, $R_1$ and $R_2$, which may be the same or different, represent a methyl or ethyl group.

Preferably, $R_3$ is an allylic group containing between 3 and 15 carbon atoms.

The following are examples of allylic tertiary amines which may be used in the present invention: N,N-dialkylprenylamine; N,N-dialkylgeranylamine or its isomer N,N-dialkylnerylamine; and N,N-dialkyl-(2,6,6-trimethyl-1-cyclohexenyl)methanamine.

In what follows, the term geranylamine denotes the mixture of the two isomers, geranyl- and nerylamine.

The vanadium-based catalysts which may be used in the present invention are, in particular, salts of vanadium having all possible oxidation numbers. In particular, among compounds in which the oxidation number is high, the following may be used: $V_2O_5$; $NH_4VO_3$; alkyl vanadates such as triethanolamine orthovanadate (TEAOV) and octadecyl orthovanadate [VO-$(OC_{18}H_{37})_3$]; vanadyl acetylacetonate [VO(AcAc)$_2$]; vanadyl sulphate (VOSO$_4$); and methylcyclohexanol orthovanadate.

According to the present invention, it is possible to use several vanadium-based catalysts simultaneously.

Moreover, these various catalysts may be used in suspension or supported. In the latter case, supports of the oxide type such as, in particular, aluminas or silicas may be used. It is also possible to use charcoals or, alternatively, resins.

The process of the invention is generally carried out in the presence of catalytic amounts of vanadium. It is understood that a person skilled in the art can adjust this amount to suit the desired rate of reaction of the amine and hydroperoxide used. Preferably, the mole ratio vanadium-based catalyst (reckoned as metal)/amine is between 0.0001 and 0.5.

According to the present invention, it is preferable to use an alkyl hydroperoxide of the formula:

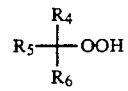

in which $R_4$, $R_5$ and $R_6$, which may be the same or different, represent: hydrogen atoms; linear or branched alkyl groups containing from 1 to 3 carbon atoms; cycloalkyl groups containing from 3 to 12 carbons atoms; or alkyl- or cycloalkylaromatic groups containing from 7 to 30 carbon atoms.

In a preferred embodiment, the hydroperoxide is chosen from cumyl, amylene, tert-butyl or cyclohexyl hydroperoxides.

The process of the invention is advantageously carried out in a solvent. In particular, the solvent may be chosen from : hydrocarbons (e.g., pentane, hexane, etc.); ethers (e.g., methyl tert-butyl ether); esters (e.g., ethyl acetate); alcohols (e.g., methanol, etc.); aromatic solvents (e.g., toluene, xylene, benzene); or halogenated solvents (e.g., methylene chloride, chlorobenzene).

The reaction is advantageously performed at a temperature between room temperature and approximately 80° C. The temperature is, in particular, adjusted to suit the solvent used.

For the invention to yield good results, it is generally preferable to work in the presence of an excess of oxidizing agent relative to the amine. However, in order to avoid oxidation of the unsaturated aldehydes formed, this excess should not be too great. In a preferred embodiment, the mole ratio of hydroperoxide/amine is between 0.1 and 5.

As stated above, the reaction product generally comprises a mixture of the aldehyde and its enamine. These two compounds may be separated and used as they are. However, the enamine formed may be readily converted to the aldehyde by hydrolysis in a dilute acid medium. Acetic acid, for example, gives very good results. This conversion is quantitative and very rapid, as illustrated in the examples. Preferably, this reaction is carried out in pH ranges close to 4.

In a particular embodiment of the invention, the process is performed in the presence of a drying agent. In particular, the drying agent may be any of the following: a 4Å molecular sieve, magnesium sulphate or sodium sulphate. As shown in the examples, the presence of such an agent enabled the reaction yields to be improved.

The process of the invention is especially well-suited to the preparation of prenal and citral, which constitute important intermediates in organic synthesis, especially in the synthesis of vitamins A and E. In the case of citral, the reaction may be outlined in the following manner:

Diethylgeranylamine (DEGA)

Citral    Enamine

These and other features and advantages of the invention will be described more fully be means of the examples which follow, which should be considered as illustrative and non-limiting.

DESCRIPTION OF THE PREFERRED EMBODIMENTS

In Examples 1 to 5, the stated yields of citral represent citral obtained directly plus the citral originating from acid hydrolysis of the citral enamine.

EXAMPLE 1

In the following order, 20 mg of $V_2O_5$, 420 mg of diethylgeranylamine (DEGA), 100 mg of a $C_{11}$ internal standard and 5 ml (6.65 g) of methylene chloride were placed in a reactor. 530 mg of 3M tert-butyl hydroperoxide in isooctane were added slowly in the course of 15 minutes at room temperature.

After 3 hours reaction at a temperature of between 27 and 29° C., the medium was cooled to 5° C. and 1 ml of water was added. The reaction products were analyzed by gas chromatography. The results are as follows:

| degree of conversion of DEGA | 93% |
|---|---|
| yield of citral | 50% |

EXAMPLE 2

The procedure was followed as in Example 1, but $VOSO_4.5H_2O$ was used in place of $V_2O_5$.

The following results were obtained:

| degree of conversion of DEGA | 76% |
|---|---|
| yield of citral | 15% |

EXAMPLE 3

420 mg (2 mmol) of DEGA, 5 ml of methylene chloride, 0.2 mmol of methylcyclohexanol orthovanadate and a $C_{11}$ internal standard were placed in a round-bottom flask. 2 mmol of 3M tert-butyl hydroperoxide in isooctane were added slowly and the temperature was maintained at 40° C.

The citral formed was assayed using gas chromatography. A 17% yield was obtained.

EXAMPLE 4

420 mg of DEGA, 5 ml of toluene, 0.2 mmol of triethanolamine orthovanadate and a $C_{11}$ internal standard were placed in a round-bottom flask. 2 mmol of 3M tert-butyl hydroperoxide in toluene were added slowly and the temperature was maintained at 20° C.

The citral formed was assayed using gas chromatography. A 17% yield was obtained.

EXAMPLE 5

The procedure followed was as in Example 4, but in the presence of a 4Å molecular sieve.

A 42% yield of citral was obtained.

EXAMPLE 6

This example illustrates the hydrolysis of the enamine to the aldehyde.

A solution in pentane containing the following was used:

| citral | 51 mg |
|---|---|
| DEGA | 199 mg |
| citral enamine | 44 mg |

This composition was stable over at least 96 hours. 10% of acetic acid was added to this solution and, after 5 to 30 minutes at room temperature, the citral present was assayed by gas chromatography with internal calibration. 85 mg of citral were obtained for an expected theoretical amount of 86 mg.

What is claimed:

1. A process for preparing an unsaturated aldehyde and its enamine, comprising oxidizing the corresponding allylic tertiary amine in the presence of an alkyl hydroperoxide and a vanadium-based catalyst wherein the allylic tertiary amine is of the formula $(R_1)(R_2)N(R_3)$ wherein $R_1$, $R_2$ and $R_3$, which may be the same or different, are chosen from $C_1$ to $C_{30}$ alkyl or $C_2$ to $C_{30}$ alkenyl groups, and may be linear, branched, substituted, unsubstituted, homocyclic, heterocyclic or containing a ring; and wherein said alkyl hydroperoxide corresponds to the formula:

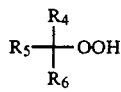

in which $R_4$, $R_5$ and $R_6$, which may be the same or different, are selected from:
hydrogen atoms;
linear or branched alkyl groups containing 1 to 3 carbon atoms;
cycloalkyl groups containing from 3 to 12 carbon atoms; and
alkyl- or cycloalkylaromatic groups containing from 7 to 30 carbon atoms.

2. The process according to claim 1, wherein $R_1$ and $R_2$ can form a ring with one another and $R_3$ represents an allylic group.

3. The process according to claim 1, wherein $R_1$ and $R_2$, which may be the same or different, are linear or branched alkyl groups containing 1 to 4 carbon atoms and are capable of forming a ring or a heterocycle with one another.

4. The process according to claim 2, wherein $R_1$ and $R_2$, which may be the same or different, represent a methyl or ethyl group.

5. The process according to claim 1, wherein $R_3$ is an allylic group containing between 3 and 15 carbon atoms.

6. The process according to claim 1, wherein said amine is selected from the group consisting of N,N-dialkylprenylamine, N,N-dialkylgeranylamine, N,N-dialkylnerylamine and N,N-dialkyl-(2,6,6-trimethyl-1-cyclohexenyl)methanamine.

7. The process according to claim 1, wherein said hydroperoxide is selected form the group consisting of cumyl, amylene, tert-butyl and cyclohexyl hydroperoxides.

8. The process according to claim 1, wherein the vanadium-based catalyst is a salt of vanadium.

9. The process according to claim 1, wherein said vanadium-based catalysts are in suspension or supported.

10. The process according to any one of claims 1, wherein one or more vanadium-based catalysts are used.

11. The process according to claim 10 wherein said vanadium-based catalyst is selected from the group consisting of $V_2O_5$; $NH_4VO_3$; vanadyl acetylacetonate; vanadyl sulphate; methylcyclohexanol orthovanadate; and an alkyl vanadate; or any combination thereof.

12. The process according to claim 11, wherein said alkyl vanadate is selected from the group consisting of triethanolamine orthovanadate and octadecyl orthovanadate.

13. The process according to claim 1, wherein the mole ratio of vanadium based catalyst to amine is between 0.0001 and 0.5.

14. The process according to claim 1, wherein the reaction is performed in the presence of a solvent.

15. The process according to claim 14, wherein said solvent is selected from hydrocarbons, ethers, esters, alcohols, aromatic solvents and halogenated solvents.

16. The process according to claim 15, wherein said solvent is selected from the group consisting of pentane, hexane, methyl tert-butyl ether, ethyl acetate, methanol, toluene, xylene, benzene, methylene chloride and chlorobenzene.

17. The process according to claim 1, wherein the mole ratio of alkyl hydroperoxide to amine is between 0.1 and 5.

18. The process according to claim 1, wherein the temperature is between room temperature and approximately 80° C.

19. The process according to claim 1, wherein the reaction is performed in the presence of a drying agent.

20. The process according to claim 10, wherein the drying agent is selected from a 4Å molecular sieve, magnesium sulphate and sodium sulphate.

21. The process according to claim 1, wherein said enamine formed is converted to said unsaturated aldehyde by hydrolysis in an acid medium.

22. The process according to claim 1, wherein the reaction product is citral or prenal.

* * * * *

UNITED STATES PATENT AND TRADEMARK OFFICE
CERTIFICATE OF CORRECTION

PATENT NO. : 5,202,497
DATED : April 13, 1993
INVENTOR(S) : Pierre CHABARDES et al.

It is certified that error appears in the above-indentified patent and that said Letters Patent is hereby corrected as shown below:

Claim 7, column 5, line 41, change "form" to --from--.

Claim 10, column 6, line 4, change "any one of claims 1" to --claim 1--.

Signed and Sealed this

Twenty-ninth Day of March, 1994

Attest:

BRUCE LEHMAN

Attesting Officer     Commissioner of Patents and Trademarks